United States Patent [19]

Terry

[11] Patent Number: 4,675,007

[45] Date of Patent: Jun. 23, 1987

[54] COUPLING DEVICE FOR ATTACHMENT TO AN END OF A CATHETER

[75] Inventor: Richard N. Terry, Clearwater, Fla.

[73] Assignee: Concept, Inc., Clearwater, Fla.

[21] Appl. No.: 783,739

[22] Filed: Oct. 3, 1985

[51] Int. Cl.⁴ .............................................. A61M 25/00
[52] U.S. Cl. ..................................... 604/283; 285/283
[58] Field of Search .............. 604/283, 165, 264, 272, 604/283, 411, 905; 285/283

[56] References Cited

U.S. PATENT DOCUMENTS

| | | | |
|---|---|---|---|
| 2,098,423 | 11/1937 | Kennedy | 285/283 |
| 3,592,192 | 7/1971 | Harautuneian | 604/165 |
| 4,006,744 | 2/1977 | Steer | 604/283 |
| 4,402,691 | 9/1983 | Rosenthal et al. | 604/411 |
| 4,449,973 | 5/1984 | Luther | 604/272 |
| 4,500,788 | 2/1985 | Kuun et al. | 604/411 |
| 4,504,269 | 3/1985 | Durand | 604/283 |

*Primary Examiner*—Stephen C. Pellegrino
*Assistant Examiner*—Mark Rooney

*Attorney, Agent, or Firm*—Frijouf, Rust & Pyle

[57] ABSTRACT

A coupling device is disclosed for attachment to an end of a catheter. The coupling device includes a tubular member having a distal and a proximal portion with the distal portion being insertable within the end of the catheter. An elongate body member having a first and a second end defines a channel which extends between the first and second ends of the body member. The channel receivably supports the proximal portion of the tubular member such that the distal portion of the tubular member extends outwardly from the first end of the body member. A catheter clamp is hingedly secured to the first end of the body member for selectively clamping the end of the catheter around the distal portion of the tubular member. The clamp is movable from a first position in which the clamp is hinged away from the distal portion of the tubular member for facilitating insertion of the distal portion of the tubular member within the end of the catheter to a second position in which the end of the catheter is clamped between the distal portion of the tubular member and the clamp.

19 Claims, 4 Drawing Figures

COUPLING DEVICE FOR ATTACHMENT TO AN END OF A CATHETER

BACKGROUND OF THE INVENTION

1. Field of the Invention

This invention relates to a coupling device for attachment to an end of a catheter. More specifically, this invention relates to a coupling device having a catheter clamp which facilitates insertion of a distal portion of a tubular member of the coupling device within an end of a catheter.

2. Information Disclosure Statement

A number of surgical procedures require the insertion of flexible catheter tubing into a patient's body. One such surgical procedure is known in the art as jejunostomy.

In recent years, there has been a renewed interest by surgeons in jejunostomy due to various factors including enhanced post-operative feeding and due to jejunostomy being a safe alternative to total parenteral nutrition.

The insertion of a flexible catheter tubing into a patient's body has been utilized in connection with surgery of the esophagus, the stomach, the duodenum, biliary tract, and surgery relative to the pancreas. Such insertion of the flexible catheter tubing by the surgeon within the patient's body has been accomplished during surgery. The insertion technique is accomplished by first inserting a rigid metal introducer needle through the skin and other tissue into a blood vessel or other body part, then threading the flexible tubing through the needle. The needle is then removed over the catheter and the catheter is left in place.

However, with the aforementioned operative procedure, a problem has existed in that usually some type of hub or connector must be secured to the exposed end of the catheter outside the patient's body such that a syringe or other medical device may be attached to the catheter tubing.

In the prior art, several techniques have been proposed in order to provide a readily attachable or detachable hub or coupling to the exposed end of the catheter. One particular coupling device includes a tubular member, the distal end of which is inserted within the exposed end of the catheter. The proximal end of the tubular member is disposed within an elongate body member and a two-part hinged clamp is clamped around the exposed end of the catheter to urge the end of the catheter into clamping abutment with the tubular member.

Another prior art connector is the Deseret connector. This connector is one piece and clamps over the catheter, but uses a second piece of tubing in the clamp itself and a metal cannula in the end of the catheter. This connector has been known to pull free when in use.

Although the prior art clamping device enables the attachment thereto of a syringe or the like, a problem has existed with the prior art device in that the hinged clamp is a separate non-integral component that must be located and placed about the end of the catheter after the insertion of the distal portion of the tubular member within the catheter. As will be apparent to those skilled in the art, it is imperative that attachment of the coupling device be preformed by the surgeon in the minimum time and the coupling device being in two parts does not facilitate this procedure.

Secondly, if the prior art catheter clamp were formed as an integral molding with the body member, it will be apparent to those skilled in the art that insertion of the distal end of the tubular member within the exposed end of the catheter would be extremely difficult because the exposed end of the catheter would have to be threaded between the space between the tubular member and the catheter clamp.

The present invention overcomes the aforementioned inadequacies of the prior art devices by providing a catheter clamp that is hingedly secured to the body member thereby not only providing a one piece coupling device, but also providing a coupling device which facilitates the insertion of the distal portion of the tubular member within the end of the catheter.

Another feature of the present invention includes the provision of a flexible guide means which extends from and is integrally molded with the catheter clamp, the flexible guide being split axially to provide a flexible guide for the attached catheter thereby inhibiting damage or occlusion of the catheter adjacent to the coupling device.

The present invention also includes a plug which is integrally formed with the elongate body member such that the plug may be inserted within the body member and may be twisted through 90° such that tabs extending from the plug coact with a flange on the elongate body member for locking the plug within the body member.

From the foregoing it will be evident that one of the important features of the present invention is that the entire coupling device is molded as a one piece construction.

Therefore, it is the primary objective of the present invention to provide a coupling device that overcomes the aforementioned inadequacies of the prior art devices and provides an improvement which significantly contributes to the ease with which a surgeon may attach the coupling device to the exposed end of a catheter or the like.

Another objective of the present invention is the provision of a coupling device in which the elongate body member in which the metal cannula or tubular member is secured may be pivoted or hinged to permit the exposed end of the catheter tubing to be placed over the cannula.

Another object of the present invention is the provision of a coupling device having a flexible guide which is integrally molded with the catheter clamp for flexibly guiding the portion of the catheter disposed adjacent to the hinged clamp in order to inhibit damage or occlusion of the catheter.

Another object of the present invention is the provision of a coupling device having a plug integrally molded with the elongate body member such that the plug is lockable within the body member by twisting the plug 90° relative to the body member and inserting the same within the body member and then twisting the plug in the reverse direction such that times extending from the plug coact with a flange on the body member.

Another object of the present invention is the provision of a coupling device which is molded as a one piece construction.

The foregoing has outlined some of the more pertinent objects of the present invention. These objects should be construed to be merely illustrative of some of the more prominent features and applications of the invention. Many other beneficial results can be attained by applying the disclosed invention in a different manner or modifying the invention within the scope of the disclosure. Particularly, with regard to the use of the invention disclosed herein, this should not be construed as being limited to coupling devices for surgical jejunostomy but should include coupling devices for attachment to any catheter or the like. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The coupling device of the present invention is defined by the appended claims with a specific embodiment shown in the attached drawings. For the purpose of summarizing the invention, the invention relates to a coupling device for attachment to an end of a catheter or the like. The invention also relates to a method of attaching an end of a catheter to a coupling device of the invention.

The coupling device includes a tubular member having a distal and a proximal portion with the distal portion being insertable within the end of the catheter. An elongate body member having a first and a second end defines a channel which extends between the first and the second ends of the body member. The channel receivably supports the proximal portion of the tubular member such that the distal portion of the tubular member extends outwardly from the first end of the body member. A catheter clamp is hingedly secured to the first end of the body member for selectively clamping the end of the catheter around the distal portion of the tubular member. The catheter clamp is movable from a first position in which the catheter clamp is hinged away from the distal portion of the tubular member for facilitating insertion of the distal portion of the tubular member within the end of the catheter. The catheter clamp is movable to a second position in which the end of the catheter is clamped between the distal portion of the tubular member and the catheter clamp.

In a more specific embodiment of the present invention, the tubular member or cannula is metal and the distal portion of the tubular member includes a first and a second end. The first end of the distal portion is cut angularly relative to the longitudinal axis of the tubular member for facilitating insertion of the first end of the distal portion within the end of the catheter. The body member is a plastic molding and the first end of the body member is disposed in a plane disposed transverse relative to the longitudinal axis of the tubular member. The proximal end of the tubular member is insert-molded into the elongate body member. "Insert-molded" describes a one step process where the tubular member is placed in a mold cavity the molding material then flows into the cavity surrounding a portion of the tubular member resulting in a single molded product. Preferably, the proximal end of the tubular member is gritglasted to improve adhesion of the body member to the tubular member. Preferably, the tubular member comprises a metal. Alternatively, the channel of the body member includes a first and second channel portion with the first channel portion having an inside diameter slightly smaller than the outside diameter of the proximal portion of the tubular member such that the first channel portion provides an "interference fit" relative to the proximal portion of the tubular member. The second channel portion includes a frusto-conical configuration for the reception therein of a syringe or the like.

The catheter clamping means includes a first clamp leaf having a first and a second end. The second end of the first clamp leaf is hingedly secured to the first end of the body member such that when the first clamp leaf is disposed in the first position thereof of the clamping means, the distance between the first end of the first clamp leaf and the first end of the distal portion is greater than the distance between the second end of the first clamp leaf and the second end of the distal portion. When the first clamp leaf is disposed in the second position thereof of the clamping means, the distance between the first end of the first clamp leaf and the first end of the distal portion is substantially the same as the distance between the second end of the first clamp leaf and the second end of the distal portion. The second clamp leaf is disposed adjacent to the first clamp leaf for cooperating with the first clamp leaf for clamping the end of the catheter around the tubular member. Hinge means is disposed between the first and second clamp leaves for hingedly securing the first and second clamp leaves together such that when the clamping means is disposed in the second position thereof, the axis of rotation of the hinge means is disposed parallel to the longitudinal axis of the tubular member.

The coupling device also includes fastening means which are disposed integrally with the clamping means for fastening the first and the second clamp leaves together when the clamping means are disposed in the second position thereof for clamping the end of the catheter between the distal portion of the tubular member and the clamping means. The first and the second clamp leaves cooperate together in the second position thereof with the fastening means fastening the leaves together such that the leaves define therebetween a bore which is coaxial with the tubular member. The bore has a diameter which is slightly smaller than the outside diameter of the catheter resulting in a pressure fit when the clamp leaves are in the second positin. The clamp leaves further include a plurality of annular bands spaced longitudinally along the length of the bore with the bands extending radially inwardly from the bore such that when the clamping means is disposed in the second position thereof the bands press radially inwardly around the end of the catheter for clamping the end of the catheter within the bore and for inhibiting removal of the end of the catheter axially relative to the tubular member.

Additionally, a coupling device includes flexible guide means which extend away from the clamping means. The guide means is disposed remote relative to and coaxial with the tubular member when the clamping means is disposed in the second position thereof such that the guide means guides the catheter away from the distal portion of the tubular member for inhibiting occlusion of and damage to the catheter. The flexible guide means is of hollow cylindrical configuration such that the catheter extends away from the distal portion of the tubular member through the guide means when the clamping means is disposed in the second position thereof. The guide means includes a first and a second end with the first end of the guide means defining longitudinal slits to permit lateral flexure of the catheter while inhibiting occlusion thereof. The second end of the guide means is integrally disposed adjacent to the clamping means.

The coupling device also includes plug means having a first and a second end. The plug means is removably disposed within the channel adjacent to the second end of the body member. Locking means are disposed adjacent to the plug means for selectively locking the plug means within the channel. The locking means includes a flange extending radially from the second end of the body member, the flange defining diametrically opposed cutaway portions. A yoke member extends from and is disposed transversely relative to the second end of the plug means with the yoke member having a first and a second end. A first and a second locking tab extend respectively from the first and second ends of the yoke member and the locking tabs extend radially inwardly such that when the locking tabs are aligned with the cutaway portions, the plug means is insertable within the channel. When the yoke member is rotated relative to the flange, the locking tabs react with the flange for locking of the plug means within the channel.

The coupling device includes a tubular member, an elongate member and a catheter clamping means all molded as a one piece construction.

The method of attaching a coupling device to an exposed end of a catheter includes the steps of pivoting the first leaf of the catheter clamping means away from the distal portion of the tubular member and inserting the first end of the distal portion of the tubular member within the exposed end of the catheter. The first leaf of the clamping means is then pivoted to the second position thereof with the first leaf abutting against the exposed end of the catheter to urge the exposed end of the catheter against the distal portion of the tubular member. The second leaf is then hinged towards the exposed end of the catheter such that the exposed end of the catheter is clamped around the distal portion of the tubular member.

The foregoing has outlined rather broadly the more pertinent and important features of the present invention in order that the detailed description that follows may be better understood so that the present contribution to the art can be more fully appreciated. Additionally, features of the invention will be described hereinafter which form the subject of the claims of the invention. It should be appreciated by those skilled in the art that the conception and the specific embodiment disclosed may be readily utilized as a basis for modifying and designing other devices for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention reference should be had to the following detailed description taken in conjunction with the accompanying drawings in which.

Similar reference characters refer to similar parts throughout the several views of the drawings.

DETAILED DESCRIPTION

Figure 1:
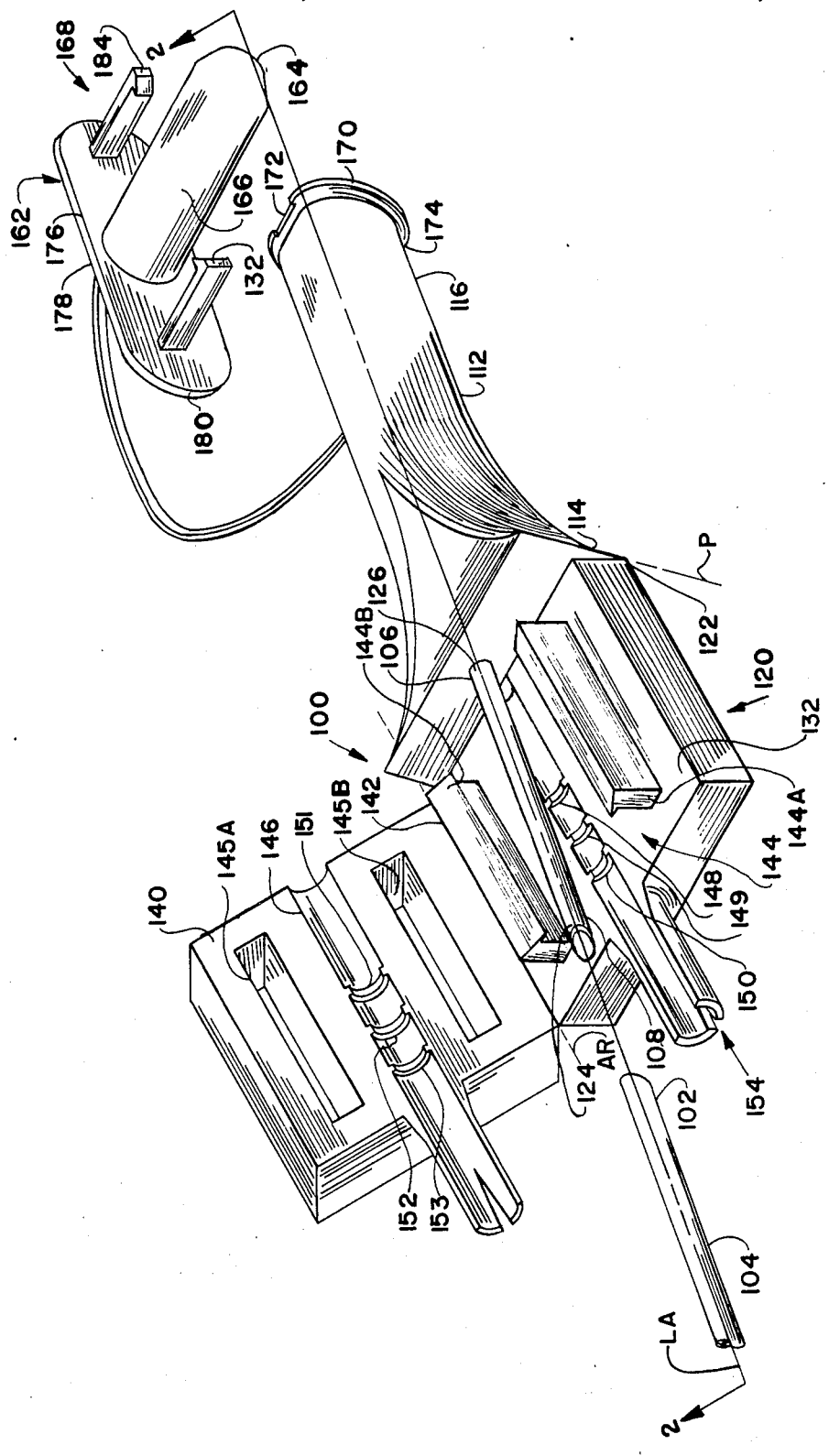
FIG. 1 is a perspective view of the coupling device according to the present invention.
Figure 2:
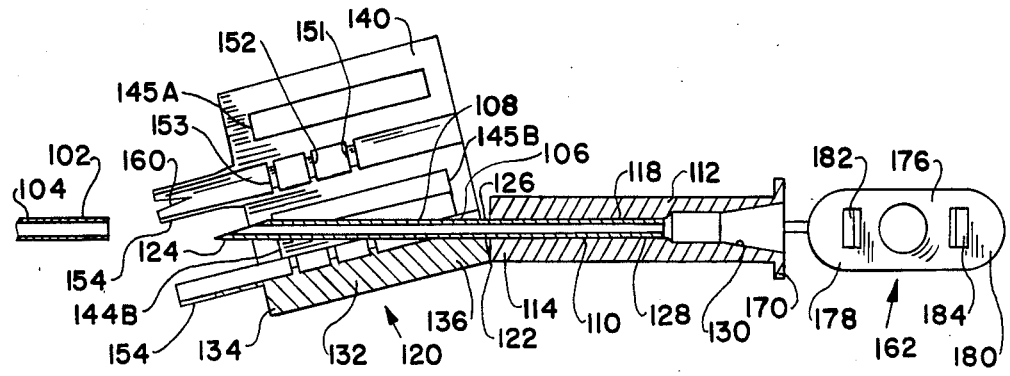
FIG. 2 is a sectional view of the coupling device taken on the line 2—2 of FIG. 1 showing the catheter clamping means disposed in the first position thereof.
Figure 3:
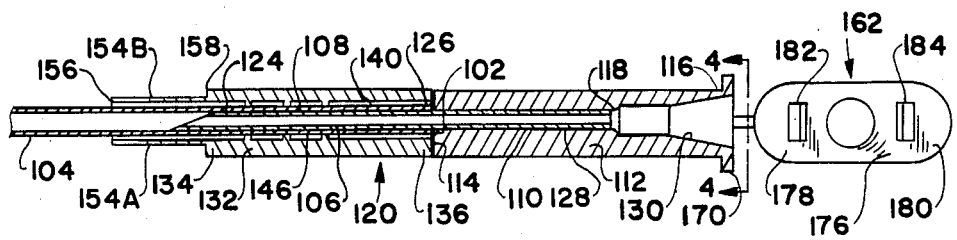
FIG. 3 is a sectional view similar to that shown in FIG. 2 but with the catheter clamping means disposed in the second position thereof and with the exposed end of the catheter clamped around the distal portion of the tubular member.

FIG. 1 shows a coupling device generally designated 100 of the present invention for attachment to an end 102 of a catheter 104. The coupling device 100 includes a tubular member 106 having a distal portion 108 and a proximal portion 110 shown in more detail in FIGS. 2 and 3 and to be described hereinafter. The distal portion 108 is insertable within the end 102 of the catheter 104. An elongate body member 112 includes a first and a second end 114 and 116 respectively. The body member 112 defines a channel 118 which extends between the first and second ends 114 and 116 respectively of the body member 112. The channel 118 receivably supports the proximal portion 110 of the tubular member 106 as shown in FIGS. 2 and 3 such that the distal portion 108 of the tubular member 106 extends outwardly from the first end 114 of the body member 112. A catheter clamping means generally designated 120 is hingedly secured at 122 to the first end 114 of the body member 112 for selectively clamping the end 102 of the catheter 104 around the distal portion 108 of the tubular member 106. The clamping means 120 is movable from a first position as shown in FIGS. 1 and 2 in which the clamping means 120 is hinged away from the distal portion 108 of the tubular member 106 for facilitating insertion of the distal portion 108 of the tubular member 106 within the end 102 of the catheter 104. The catheter clamping means 120 is then movable to a second position thereof as shown in FIG. 3 in which the end 102 of the catheter 104 is clamped between the distal portion 108 of the tubular member 106 and the clamping means 120.

Preferably, the tubular member or cannula 106 is of metal. The distal portion 108 of the tubular member 106 includes a first and a second end 124 and 126 respectively. The first end 124 of the distal portion 108 is cut angularly relative to the longitudinal axis of the tubular member 106 for facilitating insertion of the first end 124 of the distal portion 108 within the end 102 of the catheter 104.

The elongate body member 112 is preferably a plastic molding and includes a first end 114 which is disposed in a plane P disposed transversely relative to the longitudinal axis LA of the tubular member 106 as shown in FIG. 1. The channel 118 of the elongate body member 112 includes a first and a second channel portion 128 and 130 respectively. The first channel portion 128 has an inside diameter slightly less than the outside diameter of the proximal portion 110 of the tubular member 106 such that the first channel portion 128 provides an interference fit relative to the proximal portion 110 of the tubular member 106. The second channel portion 130 as shown particularly with reference to FIGS. 2 and 3 includes a frusto-conical configuration for the reception therein of a syringe or the like (not shown) or a plug to be described hereinafter.

Alternatively, proximal end portion 110 of tubular member 106 is insert-molded into elongate body member 112. Preferably, tubular member 106 is metal with the proximal end portion 110 grit-blasted to provide a roughened surface to increase the grip of elongate body member 112 on the proximal end portion.

The catheter clamping means 120 also includes a first clamp leaf 132 having a first and second end 134 and 136 respectively. The second end 136 of the first clamp leaf 132 is hingedly secured at 122 to the first end 114 of the body member 112 such that when the first clamp leaf 132 is disposed in the first position of the clamping means 120, as shown in FIGS. 1 and 2, the distance between the first end 134 of the first clamp leaf 132 and the first end 124 of the distal portion 108 is greater than the distance between the second end 136 of the first clamp leaf 132 and the second end 126 of the distal portion 108. When the first clamp leaf 132 is disposed in the second position thereof of the clamping means 120 as shown in FIG. 3, the distance between the first end 134 of the first clamp leaf 132 and the first end 124 of the distal portion 108 is substantially the same as the distance between the second end 136 of the first clamp leaf 132 and the second end 126 of the distal portion 108. A second clamp leaf 140 is disposed adjacent to the first clamp leaf 132 for cooperating with the first clamp leaf 132 for clamping the end 102 of the catheter 104 around the tubular member 106. A hinge means 142 shown in FIG. 1 is disposed between the first and second clamp leaves 132 and 140 respectively for hingedly securing the first and second clamp leaves 132 and 140 together such that when the clamping means 120 is disposed in the second position thereof, the axis of rotation AR of the hinge means 142 is disposed parallel to the longitudinal axis LA of the tubular member 106.

The coupling device 100 also includes fastening means generally designated 144 which are disposed integrally with the clamping means 120 for fastening the first and second clamp leaves 132 and 140 respectively together when the clamping means 120 is disposed in the second position thereof for clamping the end 102 of the catheter 104 between the distal portion 108 of the tubular member 106 and the clamping means 120. More specifically, the fastener means 144 includes a first and a second elongate tab 144a and 144b respectively which extend through and lockably cooperate with slots 145a and 145b respectively defined by the second clamp leaf 140 when the clamp means 120 is disposed in the second position thereof. The first and second clamp leaves 132 and 140 respectively cooperate together in the second position thereof as shown in FIG. 3 with the fastening means 144 fastening the leaves 132 and 140 together such that the leaves 132 and 140 define therebetween a bore 146 which is coaxial with the tubular member 106.

The bore 146 is of a diameter which is substantially the same as the outside diameter of the catheter 104 and the clamp leaves 132 and 140 also include a plurality of annular bands 148, 149, 150, 151, 152 and 153 which extend radially inwardly from the walls of the bore 146 such that when the clamping means 120 is disposed in the second position as shown in FIG. 3, the bands 148 to 153 press radially inwardly around the end 102 of the catheter 104 for clamping the end 102 of the catheter 104 within the bore 146 and for inhibiting removal of the end 102 of the catheter 104 axially relative to the tubular member 106.

As shown in FIGS. 1, 2 and 3 flexible guide means generally designated 154 extend away from the clamping means 120. The guide means 154 are disposed remote relative to and coaxial with the tubular member 106 when the clamping means 120 is disposed in the second position as shown in FIG. 3 such that the guide means 154 guide the catheter 104 away from the distal portion 108 of the tubular member 106 for inhibiting occlusion of and damage to the catheter. More specifically, the flexible guide means 154 includes a first and a second guide portion 154a and 154b respectively which extend from and are molded integrally with the first and second clamp leaves 132 and 140 respectively. The guide portions 154a and 154b cooperate together when the clamping means 120 are disposed in the second position as shown in FIG. 3 for defining a hollow cylindrical configuration such that the catheter 104 extends away from the distal portion 108 of the tubular member 106 through the guide means 154 when the clamping means 120 is disposed in the second position. The guide means 154 include a first and a second end 156 and 158 respectively with the first end 156 of the guide means 154 defining longitudinal split means 160 to permit lateral flexure of the catheter while inhibiting occlusion thereof. The second end 158 of the first and second guide portions 154a and 154b are integrally disposed adjacent to the first and second leaves 132 and 140 respectively.

Figure 4:
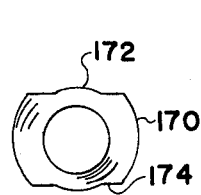
FIG. 4 is a sectional view taken on the line 4—4 of FIG. 3 showing the cutaway portions of the flange of the elongate body member.
Figure 5:
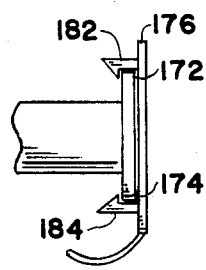
FIG. 5 shows the plug inserted within the second channel portion and the tabs engaging the flange.
Figure 6:
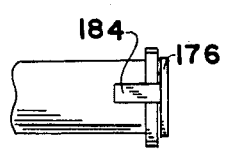
FIG. 6 is similar to the view shown in FIG. 5 but shows the plug having been twisted through 90° to lock the same relative to the elongated body member.

The coupling device 100 also includes plug means generally designated 162 having a first and a second end 164 and 166 respectively. The plug means 162 is removably disposed within the second channel portion 130 adjacent to the second end 116 of the body member 112. A locking means generally designated 168 and shown in more detail in FIGS. 4, 5 and 6 is disposed adjacent to the plug means 162 for selectively locking the plug means 162 within the second channel portion 130. More specifically, the locking means 168 includes a flange 170 which extends radially from the second end 116 of the body member 112. The flange 170 defines diametrically opposed cutaway portions 172 and 174 respectively as shown in FIG. 4. A yoke member 176 extends from and is disposed transversely relative to the second end 166 of the plug means 162. The yoke member 176 has a first and a second end 178 and 180 respectively. A first and a second locking tab 182 and 184 respectively extend respectively from the first and second ends 178 and 180 of the yoke member 176 with the locking tabs 182 and 184 extending radially inwardly such that when the locking tabs 182 and 184 are aligned with the cutaway portions 172 and 174 the plugs means 162 is insertable within the second channel portion 130 and when the yoke member 176 is rotated through 90° relative to the flange 170, the locking tabs 182 and 184 react with the flange 170 for locking the plug means 162 within the second channel portion 130.

An important feature of the present invention resides in the provision of the tubular member, elongated body member and clamping means which are integrally molded of plastics material.

In use of the coupling device 100 of the present invention, when the surgeon has removed the introducer needle (not shown) by sliding the same along and over the length of the catheter 104, the surgeon then takes the coupling device 100 of the present invention and pivots the catheter clamping means 120 to the first position thereof as shown in FIG. 2. The surgeon then inserts the first end 124 of the distal portion 108 of the tubular member or cannula 106 into the exposed end 102 of the catheter 104 sliding the end 102 of the catheter 104 along the distal portion 108 until the end 102 of the catheter 104 abuts against the first end 114 of the elongate body member 112. The first clamp leaf 132 is then pivoted towards the distal portion 108 of the tubular member 106 such that the bands 148, 149 and 150 abut against the exposed end 102 of the catheter 104 to urge the catheter 104 against the distal portion 108 of the tubular member 106. The second clamp leaf 140 is then pivoted towards the exposed end 102 of the catheter 104 until the bands 151, 152 and 153 react with and clamp the exposed end 102 of the catheter 104 around the distal portion 108 of the tubular member 106 and the fastening means 144 fasten the first and second leaves 132 and 140 together in the second position thereof of the clamping means 120 as shown in FIG. 3. With the coupling device 100 disposed in the second position shown in FIG. 3, the exposed end 102 of the catheter 104 is securely connected to the coupling device 100 such that axial movement of the end 102 of the catheter 104 is inhibited relative to the coupling device 100. Furthermore, the flexible guide means 154 guides the portion of the catheter adjacent to the clamping means 120 thereby inhibiting occlusion and damage to that portion of the catheter due to the longitudinal split means 160 of the flexible guide means 154.

The integrally formed plug means 162 is secured within the second channel portion 130 of the elongated body member 112 by inserting the plug means 162 within the second channel portion 130 and turning the plug means 162 through 90° to twist the first and second locking tabs 182 and 184 into engagement with the flange 170 disposed at the second end 116 of the body member 112.

An important feature of the present invention resides in the provision of a coupling device of unitary construction which enables a surgeon to quickly attach thereto an exposed end of a catheter, the attachment being facilitated by the pivotal disposition of the clamping means relative to the elongate body member.

The present disclosure contains that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be reorted to without departing from the spirit and scope of the invention.

What is claimed is:

1. A coupling device for attachment to an end of a catheter, said device comprising:
    a tubular member having a distal portion and a proximal portion, with said distal portion being insertable within the end of the catheter to position in use the end of the catheter around said distal portion of said tubular member;
    an elongate body member having a first and a second end;
    said elongate body member defining a channel extending between said first end and said second end of said elongate body member;
    said channel receivably supporting said proximal portion of said tubular member such that said distal portion of said tubular member extends outwardly from said first end of said elongate body member;
    a catheter clamping means for selectively clamping in use the end of the catheter positioned around said distal portion of said tubular member;
    said catheter clamping means being hingedly secured by a first hinge to said first end of said elongate body member to enable said catheter clamping means to move from a first position in which said catheter clamping means is hinged away from said distal portion of said tubular member for facilitating insertion of said distal portion of said tubular member with the end of the catheter and to move to a second position in which said distal portion of said tubular member is received by said catheter clamping means; and
    said catheter clamping means including a second hinged portion such that in use upon folding said second hinge portion forces said catheter clamping means into contact with the end of the catheter positioned around said distal portion of said tubular member when said first hinge is at said second position thereby clamping and ncoupling the end of the catheter with said distal portion of said tubular member.

2. A coupling device as set forth in claim 1 wherein said tubular member is metal.

3. A coupling device as set forth in claim 1, wherein said distal portion of said tubular member includes a first and a second end, said first end of said distal portion being cut angularly relative to the longitudinal axis of said tubular member for facilitating insertion of said first end of said distal portion within the end of the catheter.

4. A coupling device as set forth in claim 1, wherein said body member is a plastic molding.

5. A coupling device as set forth in claim 1, wherein said first end of said body member is disposed in a plane disposed transverse relative to the longitudinal axis of said tubular member.

6. A coupling device as set forth in claim 1, wherein said channel includes a first and a second channel portion, said first channel portion having an inside diameter slightly less than the outside diameter of said proximal portion of said tubular member such that said first channel portion provides an interference fit relative to said proximal portion of said tubular member.

7. A coupling device as set forth in claim 6, wherein said second channel portion includes a frusto-conical configuration.

8. A coupling device as set forth in claim 1 wherein said channel includes a first and second channel portion with said first channel portion providing an insert-moulded fit relative to said proximal portion of said tubular member.

9. A coupling device as set forth in claim 8, wherein said proximal tubular member is grit-blasted to provide an enhanced grip within said first channel portion.

10. A coupling device as set forth in claim 8, wherein said second channel portion is a frusto-conical configuration.

11. A coupling device as set forth in claim 3, wherein said catheter clamping means includes:
    a first clamp leaf having a first and a second end, said second end of said first clamp leaf being hingedly secured to said first end of said body member such that when said first clamp leaf is disposed in said first position of said clamping means, the distance between said first end of said first clamp leaf and said first end of said distal portion is greater than the distance between said second end of said first clamp leaf and said second end of said distal portion and when said first clamp leaf is disposed in said second position of said clamping means, the distance between said first end of said first clamp leaf and said first end of said distal portion is substantially the same as the distance between said second end of said first clamp leaf and said second end of said distal portion;

a second clamp leaf disposed adjacent to said first clamp leaf for cooperating with said first clamp leaf for clamping the end of the catheter around said tubular member;

hinge means disposed between said first and second clamp leaves for hingedly securing said first and second clamp leaves together such that when said clamping means is disposed in said second position, the axis of rotation of said hinge means is disposed parallel to the longitudinal axis of said tubular member.

12. A coupling device as set forth in claim 11, further including:

fastening means disposed integrally with said clamping means for fastening said first and second clamp leaves together when said clamping means is disposed in said second position for clamping the end of the catheter between said distal portion of said tubular member and said clamping means.

13. A coupling device as set forth in claim 12, wherein said first and second clamp leaves cooperate together in said second position with said fastening means fastening said leaves together such that said leaves define therebetween a bore which is coaxial with said tubular member.

14. A coupling device as set forth in claim 13, wherein said bore has a diameter which is slightly smaller than the outside diameter of the catheter, said clamp leaves further including:

a plurality of annular bands spaced longitudinally along the length of said bore, said bands extending radially inwardly from said bore such that when said clamping means is disposed in said second position said bands press radially inwardly around the end of the catheter for clamping the end of the catheter within said bore and for inhibiting removal of the end of the catheter longitudinally relative to said tubular member.

15. A coupling device for attachment to an end of a catheter, said device comprising:

a tubular member having a distal portion and a proximal portion, with said distal portion being insertable within the end of the catheter to position in use the end of the catheter around said distal portion of said tubular member;

an elongate body member having a first and a second end;

said elongate body member defining a channel extending between said first end and said second end of said elongate body member;

said channel receivably supporting said proximal portion of said tubular member such that said distal portion of said tubular member extends outwardly from said first end of said elongate body member;

a catheter clamping means for selectively clamping in use the end of the catheter positioned around said distal portion of said tubular member;

said catheter clamping means being hingedly secured by a first hinge to said first end of said elongate body member to enable said catheter clamping means to move from a first position in which said catheter clamping means is hinged away from said distal portion of said tubular member for facilitating insertion of said distal portion of said tubular member with the end of the catheter and to move to a second position in which said distal portion of said tubular member is received by said catheter clamping means;

said catheter clamping means including a second hinged portion such that in use upon folding said second hinge portion forces said catheter clamping means into contact with the end of the catheter positioned around said distal portion of said tubular member when said first hinge is at said second position thereby clamping and coupling the end of the catheter with said distal portion of said tubular member; and flexible guide means extending away from said clamping means, said guide means being disposed remote relative to and coaxial with said tubular member when said clamping means is disposed in said second position such that said guide means guide the catheter away from said distal portion of said tubular member for inhibiting occlusion and damage to the catheter.

16. A coupling device as set forth in claim 15, wherein said flexible guide means is of hollow cylindrical configuration such that the catheter extends away from said distal portion of said tubular member through said guide means when said clamping means is disposed in said second position, said guide means having a first and a second end, said first end of said guide means defining longitudinal split means to permit lateral flexure of the catheter while inhibiting occlusion thereof, said second end of said guide means being integrally disposed adjacent to said clamping means.

17. A coupling device for attachment to an end of a catheter, said device comprising:

a tubular member having a distal portion and a proximal portion, with said distal portion being insertable within the end of the catheter to position in use the end of the catheter around said distal portion of said tubular member;

an elongate body member having a first and a second end;

said elongate body member defining a channel extending between said first end and said second end of said elongate body member;

said channel receivably supporting said proximal portion of said tubular member such that said distal portion of said tubular member extends outwardly from said first end of said elongate body member;

a catheter clamping means for selectively clamping in use the end of the catheter positioned around said distal portion of said tubular member;

said catheter clamping means being hingedly secured by a first hinge to said first end of said elongate body member to enable said catheter clamping means to move from a first position in which said catheter clamping means is hinged away from said distal portion of said tubular member for facilitating insertion of said distal portion of said tubular member with the end of the catheter and to move to a second position in which said distal portion of said tubular member is received by said catheter clamping means;

said catheter clamping means including a second hinged portion such that in use upon folding said second hinge portion forces said catheter clamping means into contact with the end of the catheter positioned around said distal portion of said tubular member when said first hinge is at said second position thereby clamping and coupling the end of the catheter with said distal portion of said tubular member; and said elongate body member and said clamping means being integrally molded of plastics material.

18. A coupling device for attachment to an end of a catheter, said device comprising:

a tubular member having a distal portion and a proximal portion, with said distal portion being insertable within the end of the catheter to position in use the end of the catheter around said distal portion of said tubular member;

an elongate body member having a first and a second end;

said elongate body member defining a channel extending between said first end and said second end of said elongate body member;

said channel receivably supporting said proximal portion of said tubular member such that said distal portion of said tubular member extends outwardly from said first end of said elongate body member;

a catheter clamping means for selectively clamping in use the end of the catheter positioned around said distal portion of said tubular member;

said catheter clamping means being hingedly secured by a first hinge to said first end of said elongate body member to enable said catheter clamping means to move from a first position in which said catheter clamping means is hinged away from said distal portion of said tubular member for facilitating insertion of said distal portion of said tubular member with the end of the catheter and to move to a second position in which said distal portion of said tubular member is received by said catheter clamping means;

said catheter clamping means including a second hinged portion such that in use upon folding said second hinge portion forces said catheter clamping means into contact with the end of the catheter positioned around said distal portion of said tubular member when said first hinge is at said second position thereby clamping and coupling the end of the catheter with said distal portion of said tubular member;

flexible guide means extending away from said clamping means, said guide means being disposed remote relative to and coaxial with said tubular member when said clamping means is disposed in said second position such that said guide means guide the catheter away from said distal portion of said tubular member for inhibiting occlusion and damage to the catheter;

plug means removably disposed within said channel adjacent to said second and of said body member; and locking means disposed adjacent to said plug means for selectively locking said plug means within said channel.

19. A method of attaching an exposed end of a catheter to a coupling device comprising providing a coupling device including a tubular member having a distan portion and a proximal portion, with the distal portion of the tubular member being insertable within the end of the catheter; an elongate body member having a first and a second end; the elongate body member defining a channel extending between the first end and the second end of the elongate body member with the channel receivably supporting the proximal portion of the tubular member such that the distal portion of the tubular member extends outwardly from the first end of the elongate body member; a catheter clamping means for selectively clamping in use the end of the catheter positioned around the distal portion of the tubular member; the catheter clamping means being hingedly secured by a first hinge to the first end of the elongate body member and including a second hinged portion; and attaching an exposed end of a catheter to a coupling device comprising:

inserting the first end of the distal portion of the tubular member within the exposed end of the catheter;

pivoting the catheter clamping means to a first position in which the catheter clamping means is hinged away from the distal portion of the tubular member for facilitating insertion of the distal portion of the tubular member with the end of the catheter;

pivoting the catheter clamping means to a second position in which the distal portion of the tubular member is alignedly received by the catheter clamping means; and folding the second hinged portion of the catheter clamping means such that the second hinge portion forces the catheter clamping means into contact with the end of the catheter positioned around the distal portion of the tubular member thereby clamping and coupling the end of the catheter with the distal portion of the tubular member.

* * * * *